United States Patent [19]

Boney

[11] 3,953,538

[45] Apr. 27, 1976

[54] ALKYLATION PROCESS STARTUP PROCEDURE

[75] Inventor: William G. Boney, Rolling Meadows, Ill.

[73] Assignee: Universal Oil Products Company, Des Plaines, Ill.

[22] Filed: Sept. 9, 1974

[21] Appl. No.: 504,409

Related U.S. Application Data

[63] Continuation-in-part of Ser. No. 340,126, March 12, 1973, abandoned.

[52] U.S. Cl. .................. 260/683.48; 260/683.15 A
[51] Int. Cl.² ......................................... C07C 3/54
[58] Field of Search ............. 260/683.15 A, 683.48, 260/683.49

[56] References Cited
UNITED STATES PATENTS

| | | | |
|---|---|---|---|
| 2,384,736 | 9/1945 | Frey | 260/683.49 |
| 2,387,162 | 10/1945 | Matuszak | 260/683.48 |
| 2,434,000 | 1/1948 | Matuszak | 260/683.49 |
| 2,450,039 | 9/1948 | Frey | 260/683.49 |
| 2,462,360 | 2/1949 | Carnell | 260/683.15 A |

*Primary Examiner*—Paul M. Coughlan, Jr.
*Attorney, Agent, or Firm*—James R. Hoatson, Jr.; Robert W. Erickson; William H. Page, II

[57] ABSTRACT

A startup procedure for an alkylation process in which a stream of an olefinic material is mixed with an acid stream and polymerized to cause formation of a polymeric diluent for the high strength acid which is initially charged to the alkylation process. This quickly lowers the strength of the acid, which results in an improved alkylate quality, during the initial period of operation in which the prior art relies on the relatively slow natural buildup of alkylation reaction by-products as a diluent.

2 Claims, 1 Drawing Figure

U.S. Patent April 27, 1976 3,953,538
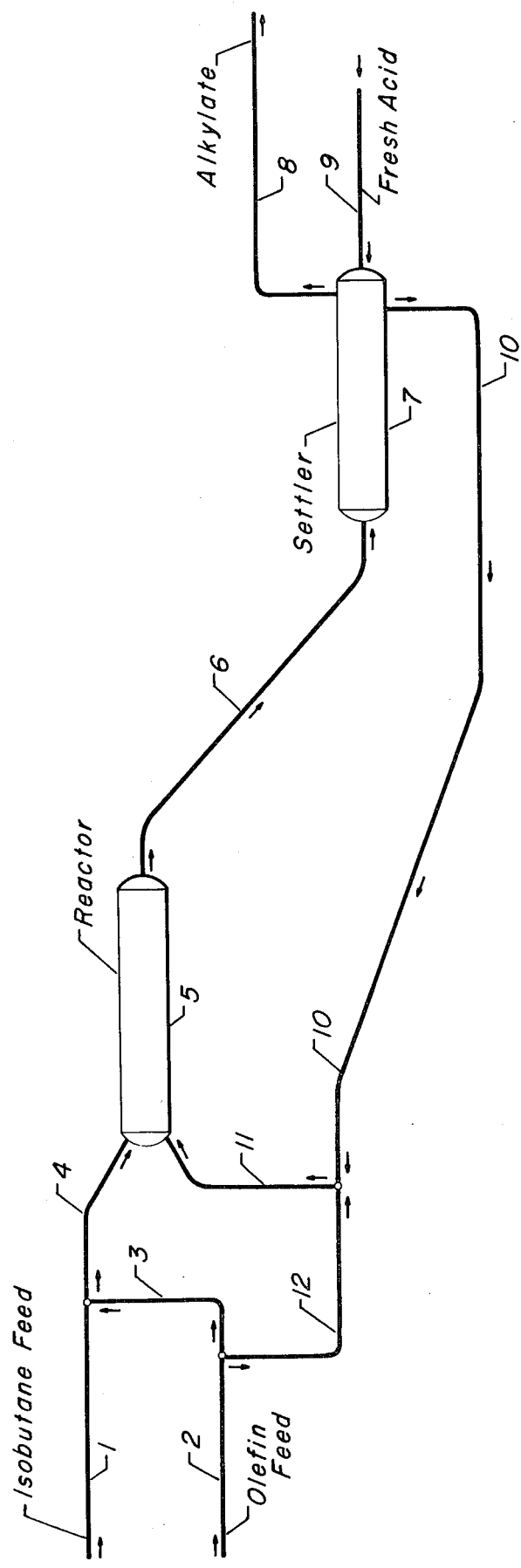

ALKYLATION PROCESS STARTUP PROCEDURE

CROSS-REFERENCE TO RELATED APPLICATIONS

This case is a Continuation-In-Part of my copending application Ser. No. 340,126 filed Mar. 12, 1973, and entitled "Alkylation Process Startup Procedure," all the teachings of which copending application are incorporated herein by this specific reference thereto.

BACKGROUND OF THE INVENTION

1. Field of the Invention

The invention relates to the mineral acid-catalyzed alkylation of hydrocarbons. Specifically, my invention relates to a startup procedure for a hydrofluoric acid-catalyzed alkylation process in which a isoparaffin is reacted with an olefin.

2. Description of the Prior Art

The prior art startup procedure comprises the steps of drying out the plant by the circulation of a dry hydrocarbon stream, charging fresh acid to the plant to provide a dry reaction zone containing the fresh acid, charging an olefin stream to the reaction zone in admixture with the feed hydrocarbon to form the product alkylate and allowing the accumulation of polymers formed as undesired by-products to dilute the acid. This method includes, of course, the normal steps of lining out distillation columns and establishing circulation through the process.

As the strength of the acid decreases due to accumulation of the polymeric diluent, the octane number and end point of the alkylate both improve. As the acid strength decreases to below 90 wt.%, it is standard procedure to begin to pass a slip stream of acid through a regeneration zone in order to maintain the acid strength between 75 and 90 percent (preferably 85–90 percent).

It is well known that olefins, such as butylene or propylene, will readily polymerize when contacted with a catalytic substance such as liquid hydrofluoric acid. The polymerization reaction is in fact so fast that major efforts have been directed toward moderation in order to produce a uniform product as described in U.S. Pat. No. 2,436,929. Likewise, U.S. Pat. No. 2,384,136 describes a method whereby the polymerization of gaseous olefins may be controlled in an alkylation process.

The olefinic feed stream to an alkylation process has been contacted with the liquid catalyst for purposes other than the conditioning of the catalyst. For instance, in U.S. Pat. No. 2,450,039, the location of a double bond in an unsaturated paraffin is shifted to form beta olefins from alpha olefins. In U.S. Pat. No. 2,387,162, the catalyst and an olefin are brought together in such a manner that reactions are limited to the creation of simple olefin-catalyst addition products such as alkyl fluorides. The object of this is the reduction of undesirable side reactions such as polymerization and the promotion of hydrogen transfer shift reactions which yield desired alkylation products after the olefin stream is admixed with a paraffinic stream.

SUMMARY OF THE INVENTION

The invention provides an improved startup procedure for use in an acid-catalyzed hydrocarbon alkylation process. In the preferred embodiment, the invention comprises the steps of introducing a fresh acid charge to the plant and starting an acid circulation through the acid circulation system of the process, passing a slipstream of the olefin feed into a line carrying the acid to cause polymerization of this slipstream and thereby forming a polymeric diluent which lowers the strength of the charged acid, passing the so-formed diluent containing acid through the acid-catalyst circulation system to create a uniform concentration of the diluent in the catalyst circulation system, and ending the diluent forming polymerization of the by-passed acid and olefin when the diluent concentration in the acid reaches a predetermined level.

By this procedure, the strength of the acid is lowered to an optimum range more rapidly than by the prior art. The alkylation process will therefore produce higher quality alkylate within a matter of days rather than produce alkylate having a reduced octane number for the first several weeks as the prior art has done. It is also within the scope of my invention that an acid stream may be passed into the olefin feed line or that a portion of the olefin feed stream may be passed into the reaction zone to form the diluent therein.

DESCRIPTION OF THE DRAWING

The preferred embodiment of my invention is illustrated in the drawing as an aid to understanding the inventive concept and interpreting the claims. As such, it is not intended to limit that interpretation to the specific flow shown as those skilled in the art will appreciate possible modifications to the operation of the described process.

In describing the drawing, it will be assumed that the process contains a charge of fresh acid-catalyst having a concentration of about 99–98 percent acid which has already been introduced into the system via acid inlet line 9. This fresh acid would be distributed in the acid circulation system which comprises the acid settler 7, lines 10, 11 and 6, and reactor 5. This acid would be slowly circulated through the system by a pump, not shown, in line 10, with the flow through line 10 being from the settler 7 to the reactor 5. Also present during startup is a flow of isobutane through the feed lines 1 and 4 into the reactor, through line 6 into the settler and then out of the settler by alkylate outlet line 8. This stream may contain some naphtha to simulate the alkylate which is to be produced and thereby allow a complete lineout of the downstream fractionation units not shown on the drawing.

After these flows have been established, a small stream of the olefin feedstock, for instance propylene, is passed through line 2 and line 12 into line 10 which is carrying the circulating stream of the acid catalyst. The acid promotes the polymerization of essentially all of the olefins and effects the formation of a heavy polymeric diluent in line 11. The resulting diluent-rich acid stream then enters the reactor. Circulation of the acid through the catalyst circulation system mixes the diluent with the bulk of the acid in reactor. This olefin injection and polymerization is continued until the average acid strength in the total system is reduced to about 86–90 weight percent, and the olefin flow is then stopped by a valve in line 12 that is not shown.

The main olefin feed stream is then passed through line 3 at its normal rate of flow and mixed with the isoparaffin entering through line 1, and this mixture is charged to the reactor through line 4. This olefin flow may alternatively have been started previous to the stoppage of the olefin injection into the acid stream. The startup procedure is now essentially completed and the alkylation process proceeds in the standard operating method of injecting the olefin and isoparaffin into the acid which results in the formation of an acid-hydrocarbon emulsion containing the product alkylate. After a controlled "soak" period in the reactor 5, the emulsion is passed into the settler 7 through line 6. Breakdown of the emulsion produces a heavier liquid acid phase which is withdrawn through line 10 and a lighter hydrocarbon phase which is withdrawn through outlet 8.

The hydrocarbon phase is passed to a separation system to recover excess isoparaffin which is returned to the process via line 1 and to prepare an alkylate product stream. As some hydrocarbon diluent is produced during normal operation, the concentration of the diluent will increase to undesirable levels unless a slipstream of acid from line 10 is passed through a regeneration zone not shown.

DETAILED DESCRIPTION OF THE INVENTION

The method of my invention is generally applicable to any acid-catalyzed alkylation process to which an olefinic hydrocarbon feed stream is charged and in which it is desired to maintain an acid-catalyst at some strength of less than 100% through the use of hydrocarbon diluents. My invention is specifically applicable to the alkylation of low boiling mono-olefins having from 2 to about 6 carbon atoms such as ethylene, propylene, butylene or pentene, with saturated branched chain isoparaffins having from 4 to about 7 carbon atoms such as isobutane or isopentane. These compounds are often reacted for the production of high octane number blending components for use in gasoline and aviation fuels. Other possible reactant combinations include an aromatic hydrocarbon with an olefin, and a paraffin or aromatic hydrocarbon with different alkylating agents such as alcohols and ethers, as for example isopropylalcohol and isopropylether. Other suitable alkylatable hydrocarbons beside isoparaffins include benzene, toluene, xylene, naphthenes, phenols, amines and thiophenes.

The alkylation reaction is promoted by the presence of a mineral acid-catalyst such as hydrofluoric acid, sulfuric acid or phosphoric acid. These acids are maintained in a liquid phase containing a minimum of water to reduce corrosion problems. The maximum amount of water normally allowed in the acid is about 5 wt.%. When fresh acid is charged to a plant, it is normally very dry and contains about 0.5 percent water or less. The catalyst may also comprise a mixture of a mineral acid and a Friedel-Crafts metal halide promoter such as aluminum chloride, aluminum bromide, boron trifluoride and other proton donors.

Alkylation conditions in general include a pressure sufficient to maintain the hydrocarbons and acid in a liquid phase, with a general range being from about 20 psig. to about 500 psig., and a more preferred range being from 100 psig. to about 250 psig. Although the alkylation reaction may be performed at temperatures from below 0°F. to about 200°F., it is preferred to operate the commercially prevalent isoparaffin-olefin alkylation process in the range of from about 50°F. to about 140°F., with 90°F. being a representaive and particularly preferred operating temperature.

Typical operating conditions in the alkylation zone include a high ratio of the concentration of the paraffinic or other alkylatable material to the concentration of the olefinic material in order to produce a high quality alkylate by encouraging monoalkylation instead of polymerization. A broad range of this ratio is from about 6 to about 20 with a preferred operating range being from 8 to 12. A second ratio which varies in competing alkylation processes is the ratio of the acid to the hydrocarbons in the total emulsion formed, that is, the ratio in the material charged to the mixing zone or reaction point. This ratio may vary widely from a high of about 10:1 to a low of about 0.5:1, but it is preferred that the isoparaffin-olefin alkylation process on which the subject startup procedure is used is operated at an acid to hydrocarbon ratio of about 2:1. Due to the ease with which low carbon number olefins polymerize in the presence of an acid catalyst, such as hydrofluoric acid, it is customary to avoid any admixing of the acid and the olefin stream until the olefin stream reaches the point at which the alkylation reaction is to occur. There are exceptions to this as mentioned in the prior art section. However, the acid-olefin contacting step of the processes mentioned therein are conducted under conditions which control or essentially eliminate polymerization. In the preferred method of operation for an alkylation process to which the invention is applied, the olefinic stream and the stream of the alkylatable hydrocarbon are both substantially acid-free and are admixed in this condition in a substantially acid-catalyst free environment. The resultant reactant mixture is then passed into the reaction zone for a controlled contacting with the acid-catalyst.

The normal startup procedure for a hydrofluoric acid alkylation plant begins with the passage of a dry hydrocarbon stream through the plant to remove water down to a level not exceeding about 50 ppm. Next, a quantity of fresh acid is charged to the plant and distributed among the vessels. Gradually flows are begun through the plant which stimulate actual operating conditions. These include passage of a high amount of the isoparaffin through the reactor, settler and product separation columns and the recycle of this isoparaffin and also the passage of a naphtha stream boiling from about 200°F. to 400°F. through the reactor, settler, and fractionation section as a synthetic alkylate. The streams are passed through the system at substantially the same conditions of temperature and pressure as are present when the process is in operation. In this manner, the process may be thought of as essentially "running" prior to the charging of any olefinic material to the process, and the introduction of the olefinic material can then be performed rather gradually and smoothly.

At this point, the prior art either gradually or relatively quickly cuts in the olefinic and paraffinic feed mixture to begin production of the alkylate in the reaction zone as the next step of the startup procedure. As a by-product of the alkylation reaction, there is formed a heavy hydrocarbon material which acts as a diluent to the catalyst stream. This by-product gradually lowers the strength of the acid stream, which is expressed herein as the weight percentage of the acid stream which is acid. It is eventually necessary to remove this diluent at a rate equal to its rate of formation. In a method well known to those skilled in the art of alkylation, a small stream of this material is passed into an acid regeneration zone, usually a small fractionation column, wherein the acid is stripped from the diluent by a stream of light hydrocarbons, such as butane. The excess diluent removed in the acid regeneration zone consists mainly of material having carbon numbers ranging from 12 to about 40 and having an average molecular weight of about 227 and an API of about 25°.

Lowering the strength of a fresh acid stream, 99.5 to 98 percent acid, to a normal operating strength of about 86 to 93 percent acid results in an increase in the octane number of alkylate produced of about 2 octane numbers. Most of the octane number improvement occurs by the time the strength of the acid in the system has been reduced to about 93 percent. It is preferred however that the strength of the acid be maintained between 85–90 wt.% acid while the system is operating. By the prior art method of gradually accumulating this material, a period of from 3 to 6 weeks is required before production of higher quality alkylate begins. It is therefore an objective of my invention to reduce the length of this period during which a lower quality alkylate is produced. The method of my invention achieves this objective by introducing a small stream of an olefinic material into a circulating catalyst stream to thereby effect the polymerization of the olefinic material and the production of a heavy organic diluent in a substantially paraffin-free environment. It is within the scope of my invention that the contacting and mixing of the acid-catalyst and the olefin to form the polymeric diluent may occur at least in part simultaneously with the initial introduction of the olefinic and isoparaffin streams into the reaction zone. However, the total desired amount of polymerization may be performed before the initiation of any substantial amount of alkylation. When this is the case, the olefinic material which is polymerized may be an unpurified stream containing a wide range of molecular species. That is to say, it is not necessary to expend a more costly purified olefinic material to perform the polymerization step. The polymerized material could therefore possibly be an unfractionated thermal cracker effluent or a light gas stream from a fluidized catalytic cracking process which contains different and higher molecular weight molecules than the olefin feed stream to the alkylation zone. The upper limit on the carbon atoms per molecule of the olefinic material which is polymerized is preferred to be from 6 to about 12.

Two of the embodiments of my invention are the injection of a stream of olefins into the recirculated catalyst and the injection of a slipstream of the catalyst into the main olefin feed stream. These two embodiments may be more clearly visualized by reference to the drawing. In the preferred embodiment, a stream of the olefin feed to the process may pass through line 12 into line 10, the main catalyst recirculation line, which then becomes line 11 leading to the reaction zone. In the alternative mode of operation, a slipstream of the recirculated catalyst may pass in the other direction through line 12 to mix with the olefinic feed passing through line 2 into line 3. In a third embodiment not shown on the drawing, a portion of the olefin feed stream may be injected directly into the reaction zone 5 at some point in which there is maintained a liquid acid phase having substantially no isoparaffins contained therein. In all three modes of operation, the olefin stream and the acid-catalyst are contacted in an environment which contains substantially no alkylatable hydrocarbons. The location of this olefin-acid contacting step may be referred to in general as a contacting or polymerization zone. The conditions of temperature and pressure which are maintained in this zone will be substantially the same as those imposed upon the reaction zone. The polymerization zone may be maintained under polymerization promoting conditions including a temperature of from about 0°F. to about 200°F., a pressure of from about 20 psig. to about 500 psig. and the presence of substantially no alkylatable hydrocarbons. The proclivity of the polymerization reaction negates the necessity for any specific effort directed toward the promotion of this reaction. The polymerization zone may therefore be operated at the pressure of the circulating acid stream being passed into the reaction zone and at ambient temperature conditions. The temperature of the acid stream being fed to the reaction zone is often lower than the desired operating temperature of the reaction zone because it is being used to remove the heat liberated in the alkylation reaction. The temperature of the acid stream may therefore be below the preferred 90°F. of the alkylation zone, but is preferably above 0°F. The polymerization reaction will itself generate heat and will raise the temperature of the acid stream. It is preferred that the temperature of the acid stream does not exceed 200°F.

The phrase "substantially no alkylatable hydrocarbons" is intended to denote a condition wherein only an unavoidable amount of the alkylatable hydrocarbon is present. With reference to an olefin feed stream, this number or concentration of alkylatable hydrocarbons, such as isoparaffins, will be very small and can refer to a concentration of less than 0.1 mole percent. In reference to the isoparaffin present in a recirculated catalyst stream of a gasoline blending component production process, the phrase is used to refer to a larger number, this number being the amount of isoparaffin which is normally dissolved in the acid phase as the acid phase leaves the settling vessel which follows the reaction vessel. This phrase is used primarily, to distinguish the mixing of the olefin and catalyst which is the subject matter of my invention from the normal alkylate producing mixing of olefin and isoparaffin in presence of acid-catalyst as occurs in the reaction zone with the previously mentioned high molar excess of the isoparaffin present. In other words, this terminology as used in the appended claims is intended to limit the position at which the mixing is to occur rather than the overall total concentration of the isoparaffin present in any given zone. The mixing and contacting referred to in the appended claims may also be distinguished from the normal mixing of acid, olefin and isoparaffin present in a typical alkylation process by the fact that it occurs for a period of only 12 to about 48 hours in duration during the startup of the alkylation process as compared to the continuous mixing of the three streams which is a necessary part of the process.

In accordance with the above description, the invention may be characterized as a startup method for a liquid phase acid-catalyzed alkylation process which comprises the steps of: passing a first hydrocarbon stream comprising olefinic normal hydrocarbons having from 2 to about 12 carbon atoms per molecule into an environment in which there are substantially no isoparaffins present and which is maintained at alkylation conditions including a pressure of from 20 psig. to about 500 psig. and a temperature of from about 50°F. to about 140°F.; mixing the first hydrocarbon stream with a liquid phase acid stream comprising at least 93 percent by weight liquid hydrofluoric acid and less than 5 percent by weight of water; effecting a polymerization of substantially all of the first hydrocarbon stream and the formation of a polymeric diluent comprising hydrocarbons having a carbon number ranging from 12 to about 40; mixing said polymeric diluent with said acid stream; and, discontinuing the mixing of the first hydrocarbon stream with the acid stream and the subsequent polymerization of the first hydrocarbon stream when the mixing of the polymeric diluent with the acid stream has reduced the weight percentage of acid in the acid stream to less than 88 percent.

The vessels labeled as reactor 5 and the settler 7 may be in a wide variety of shapes and configurations as is known to the art. Different geometrical or physical arrangements of these vessels or other lines are therefore foreseen, and terms such as reactor, settler, reaction zone and settling zone should therefore be treated broadly with full deference to the diversity of the prior art.

I claim as my invention:

1. A start-up method for a liquid phase hydrofluoric acid-catalyzed alkylation process wherein a quantity of liquid hydrofluoric acid catalyst containing less than 5 wt.% water is retained within an alkylation zone which comprises the steps of:
    a. forming a first stream of hydrofluoric acid by removing a stream of the hydrofluoric acid catalyst retained in the alkylation zone;
    b. passing a hydrocarbon stream comprising olefinic normal hydrocarbons having from 2 to about 12 carbon atoms per molecule into an environment in which there are substantially no isoparaffins present and which is maintained at a pressure of from 20 psig. to about 500 psig. and a temperature of from about 50°F. to about 140°F.;
    c. admixing the hydrocarbon stream with the first hydrofluoric acid stream and effecting a polymerization of substantially all of the hydrocarbon stream and the formation of a polymeric diluent comprising hydrocarbons having a carbon number ranging from 12 to about 40;
    d. admixing the polymeric diluent with the first hydrofluoric acid stream and effecting the formation of a second hydrofluoric acid stream containing a lower weight percentage of hydrofluoric acid than the first hydrofluoric acid stream;
    e. admixing the second hydrofluoric acid stream with the hydrofluoric acid catalyst retained in the alkylation zone, and effecting a reduction in the weight percentage of hydrofluoric acid in the hydrofluoric acid catalyst retained in the alkylation zone; and
    f. continuing the polymerization of the hydrocarbon stream in step (c) until the average acid strength in the hydrofluoric acid retained in the alkylation zone is reduced to about 86 to 90 wt.%.

2. A hydrofluoric acid-catalyzed alkylation process which comprises the steps of:
    a. admixing a first olefinic hydrocarbon stream comprising mono-olefins having from 2 to about 6 carbon atoms per molecule with an alkylatable hydrocarbon stream comprising isoparaffins having from 4 to 7 carbon atoms per molecule and effecting the formation of a reactant mixture which is substantially free of hydrofluoric acid;
    b. passing the reactant mixture into a reaction zone which contains a quantity of liquid phase hydrofluoric acid catalyst comprising less than 5 wt.% water and which is maintained under alkylation conditions, effecting the reaction of the mono-olefins with the isoparaffins and the production of high-octane gasoline blending components;
    c. effecting the formation of a second olefinic hydrocarbon stream by diverting a portion of the first olefinic hydrocarbon stream, and passing the second olefinic hydrocarbon stream into a polymerization zone maintained under conditions including a temperature of from 0°F. to about 200°F. and a pressure of from about 20 psig. to about 500 psig. and in which there are substantially no isoparaffins present;
    d. contacting the second olefinic hydrocarbon stream with liquid hydrofluoric acid and effecting a polymerization of essentially all of the second olefinic hydrocarbon stream and the formation of a polymeric diluent;
    e. admixing the polymeric diluent with the hydrofluoric acid catalyst contained with in the reaction zone and effecting a reduction in the weight percentage of hydrofluoric acid in the hydrofluoric acid catalyst contained in the reaction zone; and,
    f. continuing the polymerization of the hydrocarbon stream in step (d) until the average acid strength in the hydrofluoric acid retained in the alkylation zone is reduced to about 86 to 90 weight percent.

* * * * *